US008815228B2

(12) United States Patent
Boutros

(10) Patent No.: US 8,815,228 B2
(45) Date of Patent: *Aug. 26, 2014

(54) ALLOPLASTIC INJECTABLE DERMAL FILLER AND METHODS OF USE THEREOF

(76) Inventor: Ayman Boutros, Great Falls, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/695,116

(22) PCT Filed: Apr. 29, 2011

(86) PCT No.: PCT/US2011/034631
§ 371 (c)(1),
(2), (4) Date: Dec. 10, 2012

(87) PCT Pub. No.: WO2011/137379
PCT Pub. Date: Nov. 3, 2011

(65) Prior Publication Data
US 2013/0089580 A1     Apr. 11, 2013

Related U.S. Application Data

(63) Continuation of application No. 12/771,524, filed on Apr. 30, 2010, now Pat. No. 8,431,141.

(51) Int. Cl.
*A61K 31/78* (2006.01)
*A61K 47/36* (2006.01)
*A61K 47/42* (2006.01)
*A61Q 19/08* (2006.01)
*A61L 27/26* (2006.01)
*A61L 27/16* (2006.01)
*A61K 9/00* (2006.01)
*A61K 8/02* (2006.01)
*A61K 9/16* (2006.01)
*A61K 8/73* (2006.01)
*A61K 8/81* (2006.01)

(52) U.S. Cl.
CPC ............ *A61L 27/16* (2013.01); *A61K 2800/91* (2013.01); *A61Q 19/08* (2013.01); *A61L 27/26* (2013.01); *A61L 2400/06* (2013.01); *A61L 2430/34* (2013.01); *A61K 9/0019* (2013.01); *A61K 8/0241* (2013.01); *A61K 9/1635* (2013.01); *A61K 8/735* (2013.01); *A61K 47/42* (2013.01); *A61K 2800/412* (2013.01); *A61K 8/8152* (2013.01); *A61K 31/78* (2013.01); *A61K 2800/654* (2013.01); *A61K 47/36* (2013.01)
USPC ........................................ 424/78.31; 424/400

(58) Field of Classification Search
CPC ....... A61K 31/78; A61K 47/36; A61K 47/42; A61K 8/0241; A61K 8/738; A61K 8/8152; A61K 9/0019; A61K 9/1635; A61K 2800/412; A61K 2800/654; A61K 2800/91; A61Q 19/08; A61L 27/26; A61L 27/16; A61L 2400/06; A61L 2430/34

USPC ............................................... 424/400, 78.31
See application file for complete search history.

(56) References Cited

U.S. PATENT DOCUMENTS

| | | | |
|---|---|---|---|
| 4,443,497 A | 4/1984 | Samejima et al. |
| 4,631,188 A | 12/1986 | Stoy et al. |
| 4,772,285 A | 9/1988 | Ksander et al. |
| 4,803,075 A | 2/1989 | Wallace et al. |
| 5,223,559 A | 6/1993 | Arraudeau et al. |
| 5,344,452 A | 9/1994 | Lemperle |
| 5,571,181 A | 11/1996 | Li |
| 5,571,182 A | 11/1996 | Ersek et al. |
| 6,231,613 B1 | 5/2001 | Greff et al. |
| 6,353,069 B1 | 3/2002 | Freeman et al. |
| 6,406,498 B1 | 6/2002 | Törmälä et al. |
| 6,436,424 B1 | 8/2002 | Vogel et al. |
| 6,636,299 B1 | 10/2003 | Miyata |
| 6,673,362 B2 | 1/2004 | Calhoun et al. |
| 6,685,963 B1 | 2/2004 | Taupin et al. |
| 6,716,251 B1 | 4/2004 | Asius et al. |
| 6,878,383 B2 | 4/2005 | Boss, Jr. et al. |
| 6,896,889 B2 | 5/2005 | Chevalier et al. |

(Continued)

FOREIGN PATENT DOCUMENTS

| | | |
|---|---|---|
| CA | 2703566 | 5/2009 |
| JP | 2002-519156 | 7/2002 |

(Continued)

OTHER PUBLICATIONS

Alijotas-Reig and Garcia-Gimenez, "Delayed immune-mediated adverse effects related to hyaluronic acid and acrylic hydrogel dermal fillers: clinical findings, long-term follow-up and review of the literature," JEADV, (2007); 1-12, European Academy of Dermatology and Venereology.

(Continued)

*Primary Examiner* — Julie Ha
(74) *Attorney, Agent, or Firm* — Hunton & Williams LLP

(57) ABSTRACT

A composition comprising an alloplastic injectable suspension for use as a dermal filler comprising a biocompatible and pliable material and a physiologically acceptable suspending agent is provided. A method of making a composition comprising an alloplastic injectable suspension for use as a dermal filler comprising a biocompatible and pliable material and a physiologically acceptable suspending agent, said method comprising admixing a biocompatible and pliable material with a physiologically acceptable suspending agent, is also provided. A method of augmenting soft tissue to provide long-term reduction of a skin defect, said method comprising stimulating collagen beneath the skin defect is further provided. In an embodiment of the method of augmenting soft tissue, the stimulation of collagen production is effected by injecting into the deep reticular dermis an a dermal filler, said dermal filler being an alloplastic injectable suspension and comprising a biocompatible and pliable material and a physiologically acceptable suspending agent.

21 Claims, No Drawings

(56) References Cited

U.S. PATENT DOCUMENTS

| | | |
|---|---|---|
| 6,949,252 B2 | 9/2005 | Mizuno et al. |
| 7,193,007 B2 | 3/2007 | Cheng et al. |
| 7,910,134 B2 | 3/2011 | Boutros |
| 8,431,141 B2 | 4/2013 | Boutros |
| 8,475,815 B2 | 7/2013 | Boutros |
| 2002/0090725 A1 | 7/2002 | Simpson et al. |
| 2002/0176893 A1 | 11/2002 | Wironen et al. |
| 2003/0099682 A1 | 5/2003 | Moussy et al. |
| 2003/0181371 A1 | 9/2003 | Hunter et al. |
| 2004/0019389 A1 | 1/2004 | Swords |
| 2004/0191323 A1 | 9/2004 | Asius et al. |
| 2005/0025708 A1 | 2/2005 | Vogel et al. |
| 2005/0053567 A1 | 3/2005 | Liu |
| 2006/0073178 A1 | 4/2006 | Giampapa |
| 2006/0100138 A1 | 5/2006 | Olsen et al. |
| 2006/0136070 A1 | 6/2006 | Pinchuk |
| 2006/0276562 A1 | 12/2006 | Park et al. |
| 2006/0280769 A1 | 12/2006 | Chu et al. |
| 2007/0067045 A1 | 3/2007 | Phan et al. |
| 2007/0071729 A1 | 3/2007 | Bernstein |
| 2007/0077292 A1 | 4/2007 | Pinsky |
| 2007/0078435 A1 | 4/2007 | Stone et al. |
| 2007/0154416 A1 | 7/2007 | Hattendorf et al. |
| 2007/0166369 A1 | 7/2007 | Neuberger et al. |
| 2007/0184087 A1 | 8/2007 | Voigts et al. |
| 2007/0212385 A1 | 9/2007 | David |
| 2007/0237741 A1 | 10/2007 | Figuly et al. |
| 2007/0298005 A1 | 12/2007 | Thibault |
| 2008/0038306 A1 | 2/2008 | David |
| 2009/0110736 A1 | 4/2009 | Boutros |
| 2010/0285078 A1 | 11/2010 | Boutros |
| 2010/0322982 A1 | 12/2010 | Boutros |
| 2011/0165210 A1 | 7/2011 | Boutros |
| 2012/0189667 A1 | 7/2012 | Boutros |
| 2012/0207792 A1 | 8/2012 | Boutros |

FOREIGN PATENT DOCUMENTS

| | | |
|---|---|---|
| KR | 960009644 | 7/1996 |
| WO | WO 2005/051444 | 6/2005 |
| WO | WO 2006/010267 | 2/2006 |
| WO | WO 2006/138563 | 12/2006 |
| WO | WO 2007/095175 | 8/2007 |
| WO | WO 2007/138269 | 12/2007 |
| WO | WO 2008/001377 | 1/2008 |
| WO | WO 2009/058883 | 5/2009 |
| WO | WO 2011/137379 | 11/2011 |

OTHER PUBLICATIONS

Anwar, M.U. and D.T. Sharpe, "Skin Nodules After Semipermanent Cosmetic Dermal Filler.," Aesth. Plast. Surg. 31: 401-402, (2007).

The American Heritage® Dictionary of the English Language, "suspension", 2009.

Cohen, et al., "Artecoll: A Long-Lasting Injectable Wrinkle Filler Material: Report of a Controlled, Randomized, Multicenter Clinical Trial of 251 Subjects," Plastic and Reconstructive Surgery, Sep. 15, 2004, pp. 964-976.

Extended European Search Report for European Patent Application No. 08845548.0, mailed Nov. 30, 2010.

Eppley, et al., "Injectable Soft-Tissue Fillers: Clinical Overview," Plastic and Reconstructive Surgery, Sep. 15, 2006, 118 (4) pp. 98-106.

Fagien, S., "Facial soft-tissue augmentation with injectable autologous and allogeneic human tissue collagen matrix (autologen and dermalogen)," Plastic and Reconstructive Surgery, Jan. 2000, 105(1):362-375; discussion 374-375.

GenBank Accession No. BAA04809 [Human collagen] (Nov. 1, 1997).

GenBank Accession No. CAA23688 [*Gallus gallus* collagen] (1981).

GenBank Accession No. CAA47387 [*Mus musculus* collagen] (1992).

Haneke, E., "Polymethyl methacrylate microspheres in collagen," Seminars in Cutaneous Medicine and Surgery, Dec. 2004, pp. 227-232.

Hotta, T., "Dermal Fillers. The Next Generation," Plastic Surgical Nursing, Jan.-Mar. 2004, vol. 24. No. 1, pp. 14-19.

International Search Report for International Application No. PCT/US2011/034631, mailed Jul. 8, 2011.

International Search Report for International Application No. PCT/US2008/081608, mailed Dec. 23, 2008.

Krukowski, et al., "Charged Beads Stimulate Bone Formation," Transactions of the 34th Annual Meeting of the Orthopedic Research Society, 1988, vol. 13, p. 49, The Orthopaedic Research Society, Atlanta, GA.

Lemperle, et al., "Soft Tissue Augmentation with Artecoll: 10-Year History, Indications, Techniques and Complications," Dermatol. Surg. 29:6: Jun. 2003, pp. 573-587.

Lemperle, et al., "ArteFill: a third-generation permanent dermal filler and tissue stimulator," Clinics in Plastic Surgery, Oct. 2006, 33, (4) pp. 551-565.

MacroPore Resorbable Technology: An Overview, Scientific Data Series in Resorbable Fixation, (2001), MacroPore, Inc.

Merriam-Webster on-line dictionary (2010) ["heteropolymer"].

Meacock et al., "The effect of polymethylmethacrylate and acrysof intraocular lenses on the posterior capsule in patients with a large capsulorrhexis," Jpn J Ophthalmol. Jul.-Aug. 2001;45(4): 348-54.

Mustacchio, et al., "A diagnostic trap for the dermatopathologist: granulomatous reactions from cutaneous microimplants for cosmetic purposes." J. Cutan Pathol (2007): 34:281-283.

Nicolau, P.J., "Long-Lasting and Permanent Fillers: Biomaterial Influence over Host Tissue Response," Plastic & Reconstructive Surg. J., 2007 vol. 119(7), p. 2271-2286.

Stuzin, J., "Restoring Facial Shape in Face Lifting: The Role of Skeletal Support in Facial Analysis and Midface Soft-Tissue Repositioning," Plastic and Reconstructive Surgery, Jan. 2007, 105(1):362-372, vol. 119, No. 1, pp. 362-376.

Odian (2004) *Principles of Polymerization*. Wiley-Interscience, p. 464.

Topaz and Neuhann-Lorenz, "Position statement of IQUAM Jul. 15, 2006," Eur. J. Plast. Surg (2007) 29:249-254.

Weiss, et al. "Autologous Cultured Fibroblast injection for Facial Contour Deformities: A Prospective, Placebo-Controlled, Phase III Clinical Trial," Dermatol. Surg., (2007), 33:263-268, The American Society for Dermatologic Surgery, Inc.

Wiest, L.G., "Historic and Anwendung der Filler zur Falternbehandlung," Hautarzt (2007) 58:244-231 English Translation of Abstract at p. 227.

Yamanaka et al., Polyubiquitination events mediate polymethylmethacylate (PMMA) particle activation of NF-kappaB pathway, J. Bio. Chem., Jul. 8, 2011, 286(27):23735-23741.

Retrieved from the internet website http://www.aafprs.org/patient/procedures/wrinkles.html, "Understanding Various Treatments of Facial Wrinkles," [Retrieved Sep. 20, 2007] p. 1-3.

Retrieved from the internet website http://www.infoplasticsurgery.com/facial/wrinkletreatment/index. html, "Wrinkles: Not All Wrinkles Were Created Equal," [Retrieved Sep. 20, 2007], p. 1-4.

Retrieved from the internet website http://www.cosmeticskin.com/skin-acnescartypes.shtml., "Acne Scar Types/Treatments," [Retrieved Sep. 21, 2007] p. 1-2.

Retrieved from the internet website http://www.drnormington.com/procedures/facial-surgery/natural-skin-fillers.asp, "Natural Skin Fillers : Collagen, Restylane, Juvederm™, Radiesse," [Retrieved Sep. 20, 2007], p. 1-2.

"Zyplast® Collagen Implant Physician Package Insert," © 2000 McGhan Medical Corporation, p. 1-2, Fremont, CA.

Retrieved from the internet website http://www.plasticsurgery.org/media/press_releases/Injectables-at-a-Glance.cfm, "Restylane and Other Injectables at a Glance," [Retrieved Sep. 20, 2007] p. 1-4.

Retrieved from the internet website http://www.virginiafacialplasticsurgery.com, "Indications and potential uses of Artefill," [Retrieved Aug. 20, 2007], p. 1-4.

Retrieved from the internet website http://www.marckernermd.com/nonsurgical_facial_fillers.php, "Fillers," [Retrieved Sep. 20, 2007], p. 1-3.

(56) References Cited

OTHER PUBLICATIONS

Retrieved from the internet website http://www.springerlink.com/content/epxlahrm171haumb/, The Value of a New Filler Material in Corrective and Cosmetic Surgery: DermaLive and DermaDeep, [Retrieved Sep. 20, 2007], vol. 25, No. 4/Jul. 2001, p. 249-255 (Abstract).

Retrieved from the internet website http://www.freshnews.com/news/biotech-biomedical/article_ 34856.html?Artes+Medical, "Artes Medical Announces FDA Approval for ArteFill as the First Non-Resorbable Injectable Wrinkle Filler to Correct Smile Lines," [Retrieved Sep. 20, 2007], p. 1-3.

Retrieved from the internet website http://www.artefill.com/consumer/about_artefill.html, "Discover ArteFill®," [Retrieved Sep. 20. 2007], p. 1-2.

Retrieved from the internet website http://www.artefill.com/consumer/about_artefill.html, "How ArteFill® Works," [Retrieved Sep. 20, 2007], p. 1-2.

Retrieved from the internet website http://www.icls.ca/html/skin-aretcoll.html, "What is Artecoll," [Retrieved Aug. 20, 2007], p. 2-4.

Retrieved from the internet website http://www.alleganandinamed.com/products/facial/us/patient/zz/ prodinfo.aspx, "Facial aesthetics—US Patients: Zyderm & Zyplast—Product Information," [Retrieved Sep. 20, 2007], p. 1-2.

AcrySof® NATURAL Product Information: Alcon Laboratories, Inc., Jul. 3, 2003.

Retrieved from the internet website http://www.plasticsurgery.org/media/press_releases/, Media Statement: Permanent Injectable for Wrinkle Reduction May Have Drawbacks: FDA General and Plastic Surgery Device Panel Recommends Approval of Artecoll®, [Retrieved Sep. 20, 2007], p. 1-2.

Retrieved from the internet website http://www.healthseakers.com/pages/wrinkles/wrinklereduction. html, "Wrinkle Reduction: FDA panel urges OK of new wrinkle treatment," Feb. 28, 2003 [Retrieved Sep. 20, 2007].

Retrieved from the internet website http://www.emedicine.com/plastic/topic 56.htm, "Facial Alloplastic Implants, Chin," May 23, 2006, [Retrieved Sep. 20, 2007], p. 1-15.

Retrieved from the internet website http://www.allenaesthiticsandlasercenter.com/captique-wrinkle-reduction.htm, "Captique Wrinkle Reduction,"[Retrieved Sep. 20, 2007], p. 1-3.

Retrieved from the internet website http://www.infoplasticsurgery.com/facial/wrinkletreatment/collagen.html, "Collagen: Wrinkle Fillers," [Retrieved Sep. 20, 2007], p. 1-3.

Retrieved from the internet website http://www.turklemd.com/face/cosmetic-injections.php, "Injectable Fillers for Lip Augmentation and Wrinkle Reduction," [Retrieved Sep. 20, 2007], p. 1-3.

Retrieved from the internet website http://www.trbchemedica.com/ang/VISMED/VismedPage3.html, Sodium Hyaluronate, [Retrieved Sep. 20, 2007], p. 1-2.

Retrieved from the internet website http://www.products.sanofi-aventis.us/hyalgam/hyalgam.html, HYALGAN® (Sodium Hyaluronate) Prescribing Information, [Retrieved Sep. 20, 2007], p. 1-10.

Retrieved from the internet website www.thelabrat.com/protocols 1X Phosphate Buffered Saline (PBS) recipe from [Retrieved May 28, 2009].

International Search Report from International Patent Application No. PCT/US2008/081608 (Dec. 23, 2008).

Written Opinion (WO) from International Patent Application No. PCT/US2008/081608 (Dec. 23, 2008).

International Preliminary Patentability Report (IPER) from International Patent Application No. PCT/US2008/081608 (May 4, 2010).

International Search Report (ISR) from International Patent Application No. PCT/US2011/034631 (Jul. 8, 2011).

Written Opinion (WO) from International Patent Application No. PCT/US2011/034631 (Jul. 8, 2011).

International Preliminary Patentability Report (IPER) from International Patent Application No. PCT/US2011/034631 (Nov. 6, 2012).

International Search Report from International Patent Application No. PCT/US2012/71288, mailed Feb. 26, 2013.

Written Opinion (WO) from International Patent Application No. PCT/US2012/71288, mailed Feb. 26, 2013.

ALLOPLASTIC INJECTABLE DERMAL FILLER AND METHODS OF USE THEREOF

RELATED APPLICATION DISCLOSURE

This application is the U.S. National Stage filing of International Application No. PCT/US2011/034631, filed Apr. 29, 2011, which claims priority of U.S. patent application Ser. No. 12/771,524, filed Apr. 30, 2010, each of which is hereby incorporated by reference in their entirety.

FIELD OF THE DISCLOSURE

This application relates to an alloplastic injectable suspension for use as a dermal filler, which produces little or no immunologic response in the host tissue. In a further aspect, this application relates to methods of use of the alloplastic injectable suspension for aesthetic indications, including wrinkle reduction and medical indications, such as amelioration of cosmetic defects.

BACKGROUND

Wrinkles of the skin, whether fine superficial lines or deeper creases, are visible signs of aging. Premature aging and its associated wrinkles may be caused by skin damage from excessive exposure to sunlight and environmental pollution, as well as muscle overuse for facial expression such as smiling and frowning. Other factors which may contribute to wrinkle formation include smoking tobacco products and exposure to cigarette smoke, poor nutrition and skin disorders.

During the aging process a loss of collagen and hyaluronic acid in the skin occurs resulting in fine wrinkles and creases as well as thinner skin. Aging-associated wrinkles are known as static wrinkles. In contrast, dynamic wrinkles are caused by repeated muscle movement when making a facial expressions resulting in skin creases and folds which remain in the absence of the facial expressions, Dynamic wrinkles include smile lines, frown lines, crow's feet, lip wrinkles and forehead creases. Sagging of the skin results in the development of wrinkles in the skin fold. For example, sagging cheeks develop wrinkles in the skin fold known as the nasolabial fold from the corners of the nose, around the sides of mouth and down to the chin.

The quest for youthful-looking skin, free of wrinkles, is centuries old. Treatment of wrinkles due to aging and skin damage must obtain a visible improvement in the skin appearance, such as a smoothing effect, for as long as possible with minimal side-effects, such as immunologic reactions. Treatment of skin defects, whether for cosmetic or medical reasons must strike a balance between achieving long-term aesthetically pleasing results, minimizing side effects or complications of the treatment procedure and the host tissue reaction thereto, and decreasing the recurrence of treatment to achieve the intended results.

Current methods of treatment of wrinkles and sagging skin range from a rhytidectomy, commonly known as a face-lift, which involves removing excess fat, tightening underlying muscles, and redraping the skin of the face and neck to minimally-invasive procedures such as laser resurfacing, chemical peels, and injection of Botulinum toxin type A (BOTOX®). Each method may not achieve the desired amelioration of a particular skin defect or only achieve a short-lived improvement, which necessitates additional treatment with the same composition or procedure or the use of a different procedure.

Injectable dermal fillers provide a noninvasive option for reducing skin defects, such as wrinkles or scars, with less recovery time than a face-lift. Injectable soft-tissue fillers raise the skin within the skin defect, which is lower or deeper than the surrounding and upon which light casts a shadow to produce a visible sign, such as the defect. The filling of soft tissue underneath the skin defect raises of the skin bringing the defect to approximately the same level as the surrounding skin to decrease the shadow.

Collagen, a naturally occurring protein which supports the skin, tendons and ligaments, has been used as a soft-tissue filler since the early 1980s for correcting contour deformities of the dermis in non-weight bearing areas. A common injectable collagen dermal filler, or implant, approved by the U.S. Food and Drug Administration (FDA), is made by extracting bovine collagen from bovine skin, which is purified and sterilized and then dispersed in a phosphate-buffered physiological saline, which contains 3% lidocaine. The collagen may be lightly cross-linked with glutaraldehyde or non-crosslinked. These types of fillers have been used to improve distensible acne scars, atrophy caused by disease or trauma, glabellar frown lines, nasolabial folds, rhinoplasty, skin graft or other surgically-induced irregularities and soft tissue defects. Prior patient skin testing is required to determine the existence of an allergy to collagen. Bovine collagen injections produce immediate results, but its amelioration of skin defects are transient, lasting only from six weeks up to six months, and also pose a risk of allergic reactions and potential connective tissue disorders.

Other collagen dermal fillers are available. Autologen is a collagen extracted from the patient's own skin, sterilized and processed into injectable form and the effects of its injection appear to last longer than bovine collagen injections, but are variable. Isolagen, is a preparation of live cloned fibroblasts, such as collagen-producing cells, which are also derived from a patient's own skin and prepared into liquid form. These live fibroblasts may improve skin defects over several months, but three injections at two-week intervals are recommended for a higher percentage of wrinkle improvement and maintenance injections may be needed. Dermalogen, is sterilized, purified and processed collagen obtained from deceased human donors. This collagen filler also may last longer than bovine collages and minimize the risk of allergic reactions and connective tissue disorders, but theoretical risk of infection transmission exists. This treatment of skin defects may require additional injections and its effects may reduce over time.

Hyaluronic acid, another skin component, also is used as a dermal filler. Animal-derived, for example, extracted from rooster combs, and non-animal hyaluronic acid skin fillers, for example, recombinantly produced hyaluronic acid or synthetically produced hyaluronic acid, are available commercially for treatment of moderate to severe (deep) facial wrinkles and folds and for adding volume around the nose and mouth and other soft tissue. Allergic reaction may occur from an injection of an animal-derived hyaluronic acid or dermal fillers in patients sensitive to avian products, as well as with the recombinantly produced hyaluronic acid in those with allergies to bacterial proteins. Although immediate correction of wrinkles and folds is achieved after injection of these hyaluronic acid soft-tissue fillers, their effects are temporary, lasting from up to six months to up to a year.

Calcium hydroxyapatite, a component of bone and teeth, is also used in an injectable dermal filler in the form of microspheres suspended in an aqueous carrier. Unlike with the above-described skin fillers, the host tissue reacts to the injected calcium hydroxyapatite microspheres to stimulate collagen production to encapsulate each foreign microsphere independently, thereby adding bulk (volume) under the skin defect to reduce its appearance. Calcium hydroxyapatite microsphere injectable dermal filler is approved for treatment of moderate to severe (deep) wrinkles and folds. The results of an injection of a suspension of calcium hydroxyapatite microspheres are reported to be immediate and longer lasting than the effects of collagen skin filler, such as from about one to two years.

Synthetic poly-lactic acid, which is biodegradable and biocompatible, is contained in microspheres in another fairly recent injectable dermal filler approved outside the United States for the correction of fine lines, wrinkles, furrow and creases. In the United States, this injectable poly-lactic acid microsphere skin filler is FDA approved for restoration and/or correction of lipoatrophy in HIV patients. The poly-lactic acid microspheres having a diameter of 2 to 50 µm the dermal filler become porous after a first phase of moderate inflammation in the host tissue, followed by a second stronger inflammation in which foreign body giant cells phagocytose the microspheres and speed up the implant's degradation. The improvement of skin defects is immediate and has been reported to endure for up to two years. The non-resorbable microspheres add permanent volume under the treated skin defect, as well as stimulate the host to produce collagen fibers around the implant. Potential adverse side effects of injected poly-lactic acid microsphere skin filler include the formation of an inflammatory granuloma and lump formation.

Another permanent microsphere-based injectable dermal filler contains larger non-resorbable microspheres made of polymethyl methacrylate (PMMA), each having a diameter of between 30 and 42 µm and a smooth surface, and a highly purified bovine collagen gel in a ratio of 20% PMMA to 80% bovine collagen. This injectable dermal filler also contains 0.3% lidocaine anesthetic solution. The diameter of solid particles may be larger, see e.g., U.S. Pat. No. 5,344,452, which is incorporated herein by reference in its entirety. Because of the collagen content of this injectable dermal filler, a skin test for collagen allergy is required. The injectable PMMA-bovine dermal filler is FDA approved as a non-resorbable aesthetic injectable implant for correction of nasolabial folds, such as smile lines. It is injected into deep dermis, hypodermis or epiperiosteally, but is difficult to use in the lips as muscle movement compress the microspheres injected in a row, or strand, to form nodules. Although immediate wrinkle improvement results from this particular injectable dermal filler, two to three additional treatments about four to eight weeks apart may be required to achieve the final desired result. Adverse side-effects include lumpiness and inflammatory granulomas. Treatment with injectable PMMA-collagen dermal filler is contraindicated in patients with known bovine allergies and lidocaine allergies, as well as those with susceptibility to keloid formation. Treatment with this dermal filler is considered permanent, not only because of the volume increase under the skin defect, but also because of the presumed life-long stimulation of collagen deposition beneath the skin defect.

The electrical charge of dermal filler microbeads appears to play a role in attracting and activating macrophages, which promotes formation of foreign body giant cells, then fibroblasts, and thereby increases the composition of new connective tissue.

Each of these methods of treatment for skin defects, such as wrinkles, scars or other deformities, provides a varying duration of effect in reducing the skin defect or stimulating host production of fibroblasts and fibrocytes, produces an immediate and/or delayed immune response, poses a risk of allergy and results in palpable or visible side-effects, such as clumping, lumping, nodule formation and granuloma formation.

Accordingly, there still exists an unmet need for compositions for long-term reduction of skin defects associated with the aging process or premature aging, such as dynamic wrinkles, static wrinkles, fine wrinkles, acne scars, surgery scars, injury scars. It is desirable that the such compositions produce a smoothing of the skin without causing an allergic reaction, an immediate inflammatory response, a delayed inflammatory response or a recurring inflammatory response in the host tissue. Also desirable are methods of producing compositions for long-term reduction of skin defects, as well as methods of using such compositions to augment soft tissue by inducing in the host tissue stimulation of collagen production fibroblast production, fibrocyte production or production of any combination thereof.

SUMMARY

A composition comprising an alloplastic injectable suspension for use as a dermal filler comprising a biocompatible and pliable material and a physiologically acceptable suspending agent is provided in an embodiment.

A method of making a composition comprising an alloplastic injectable suspension for use as a dermal filler comprising a biocompatible and pliable material and a physiologically acceptable suspending agent, said method comprising admixing a biocompatible and pliable material with a physiologically acceptable suspending agent, is also provided in another embodiment.

A method of augmenting soft tissue to provide long-term reduction of a skin defect, said method comprising stimulating collagen production, fibroblast production, fibrocyte production or production of any combination thereof, beneath the skin defect, is further provided in an embodiment.

A method of reducing wrinkles and scars, said method comprising stimulating collagen production, fibroblast production, fibrocyte production or production of any combination thereof, beneath the skin defect, is further provided in an embodiment.

In an embodiment of the methods of augmenting soft tissue and reducing wrinkles and scars, the stimulation of collagen production fibroblast production, fibrocyte production or production of any combination thereof is effected by injecting into the superficial dermis, deep dermis, hypodermis, subcutaneous tissue or epiperiosteally (near and above a bone) a dermal filler, said dermal filler being an alloplastic injectable suspension and comprising a biocompatible and pliable material and a physiologically acceptable suspending agent These and other embodiments will become readily apparent to those skilled in the art upon review of the detailed description that follows.

DETAILED DESCRIPTION

For the purposes of promoting an understanding of the embodiments described herein, reference will be made to embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition.

A "copolymer" is a polymer comprising more than one monomer in the polymer chain. The constituent monomers may be arranged in various ways, including alternating copolymers, periodic copolymers, statistical copolymers, random copolymers, graft copolymers, block copolymers, stereoblock copolymers, and other arrangements known in the art. Copolymers may be linear or branched, which includes star copolymers, brush copolymers, and comb copolymers, and other branched copolymer structures that are known in the art. For example, the molar ratio between the substituent monomers in a copolymer may be about 1:1000, about 1:100, about 1:10, about 1:9, about 1:8, about 1:7, about 1:6, about 1:5, about 1:4, about 1:3, about 1:2, about 1:1, or other fractional or whole-number ratios, or between any of the foregoing values.

An exemplary copolymer is a phenylethyl acrylate and phenylethyl methacrylate copolymer, an example of which is the copolymer used in AcrySof MA60BM intraocular lenses (Alcon Laboratories) and for other uses such as fabrication of porous membranes, as well as in pharmaceuticals. According to certain embodiments of the invention, the copolymer may be cross-linked. According to an embodiment of the invention, the cross-linking agent may be 1.4 butanediol diacrylate.

Additional exemplary cross-linking agents may be any terminally ethylenically unsaturated compound having more than one unsaturated group, i.e., a multiplicity of unsaturated groups. Certain exemplary terminally ethylenically unsaturated compounds are disclosed in U.S. Pat. No. 5,741,923. Other exemplary cross-linking agents include, but are not limited to, the following: ethylene glycol diacrylate or dimethacrylate, diethylene glycol diacrylate or dimethacrylate, triethylene glycol diacrylate or dimethacrylate, tetraethylene glycol diacrylate or dimethacrylate, polyethylene glycol diacrylate or dimethacrylate, trimethylolpropane triacrylate or trimethacrylate, bisphenol A diacrylate or dimethacrylate, ethoxylated bisphenol A diacrylate or dimethacrylate, pentaerythritol tri- and tetra-acrylate or methacrylate, tetramethylene diacrylate or dimethacrylate, methylene bisacrylamide or methacrylamide, dimethylene bisacrylamide or methacrylamide, N,N'-dihydroxyethylene bisacrylamide or methacrylamide, hexamethylene bisacrylamide or methacrylamide, decamethylene bisacrylamide or methacrylamide, divinyl benzene, vinyl methacrylate, allyl methacrylate, etc. Additional exemplary cross-linking agents include 1,3-bis(4-methacryloyl oxyalkyl)tetra disiloxane and similar poly(organo-siloxane) monomers set forth in U.S. Pat. No. 4,153,641. Another group of exemplary cross-linking agents are the resonance-free di(alkylene tertiary amine) cyclic compounds, e.g., N,N'-divinyl ethylene urea, as disclosed in U.S. Pat. No. 4,436,887. Further exemplary cross-linking agents include di- or polyvinyl ethers of di- or polyvalent alcohols such as ethylene glycol divinyl ether. The foregoing publications are hereby incorporated by reference in their entireties.

A composition comprising an alloplastic injectable suspension for use as a dermal filler comprising a biocompatible and pliable material and a physiologically acceptable suspending agent is provided in an embodiment.

In an embodiment, the biocompatible and pliable material is a copolymer of an unsubstituted acrylate monomer and a substituted acrylate monomer.

In a further embodiment of this copolymer, the substituted acrylate monomer is substituted with a methyl group. The copolymer of an unsubstituted acrylate monomer and a substituted acrylate monomer is not absorbable or degradable by the body and is inert, and unrecognized by the immune system. The immunologic inertness of the copolymer does not allow for formation of inflammatory granuloma and scarring. The copolymer of an unsubstituted acrylate monomer and a substituted acrylate monomer is pliable, a characteristic that is important for skin applications. The copolymer material also is hydrophobic, which may be beneficial for expansion of the skin in areas where wrinkles form. The copolymer of an unsubstituted acrylate monomer and a substituted acrylate monomer may have a tint for easier removal, if needed, such as in cases of a face lift after injection of material years later.

In another embodiment of the copolymer of an unsubstituted acrylate monomer and a substituted acrylate monomer, the substituted acrylate monomer may be substituted with a functional group other than a methyl group. Substituent groups may include those groups that are unreactive (or a potentially reactive group, which is rendered inaccessible to reaction) and of the same or equivalent steric size as a methyl group. However, the steric size of a substituent group is not limited to one similar to a methyl group. For example, other alkyl group derivatives may impart the same type of pliability property, e.g., one to four (even five) carbon chain lengths (methyl, ethyl, propyl, isopropyl, butyl, tert-butyl, pentyl) acrylate derivatives. Such derivatives also are widely available commercially. An alternative substituent group for the substituted acrylate monomer may be chlorine, which takes up about the same steric space as a methyl group. Chlorine may be a reactive group, but its potential reactivity may not interfere with its use as a substituent group for the substituted acrylate monomer because the solid non-dispersed state of the copolymer would render the chlorine group inaccessible, i.e., hidden from reaction with another reactive group. Nitrile groups are another possible substituent for the substituted acrylate monomer, as they also may be similar in size to a methyl group. A nitrile group potentially may be reactive, however this potential reactivity may not impede its use as a substituent for the same reasons as described for the chlorine group. Other halogens may be suitable for use in substitution of the substituted acrylate monomer, as well. Substitution of the substituted acrylate monomer with a phenyl group may also impart pliability to the copolymer. A phenyl substituent may be used if no pi-stacking of the phenyl groups occurs, i.e., stacking on top of each other.

In another embodiment of the composition comprising an alloplastic injectable suspension, the biocompatible and pliable material is an acrylate/methacrylate copolymer.

In a further embodiment of the composition comprising an alloplastic injectable suspension, the acrylate/methacrylate copolymer is a solid. In an embodiment, the solid may be a non-porous microbead. In a still further embodiment, the solid may be a powder. In another embodiment, the solid may be a microsphere. In a further embodiment of the alloplastic injectable suspension, the solid has a diameter of about 10μ to about 100μ.

In accordance with various embodiments of the present invention, the acrylate/methacrylate copolymer is in the form of particles each having a diameter of less than about 100μ. According to a preferred embodiment, the diameter of each particle is less than about 10μ. In accordance with another preferred embodiment, the particles each have a diameter of about 0.01μ to about 10μ. In another preferred embodiment, the particles each have a diameter of about 0.1μ to about 5μ.

In an embodiment of the alloplastic injectable suspension, the physiologically acceptable suspending agent is resorbable, such as it is absorbed by the body, but not degraded.

The physiologically acceptable suspending agent may be a buffered physiological solution in another embodiment of the alloplastic injectable suspension. In an alternative embodiment, the physiologically acceptable suspending agent comprises cross-linked sodium hyaluronate. In a further alternative embodiment, the physiologically acceptable suspending agent comprises a non cross-linked sodium hyaluronate. In embodiments wherein the buffered physiological solution comprises non cross-linked or cross-linked sodium hyaluronate as a suspending agent, the sodium hyaluronate may comprise from about 10% to about 80% of the buffered physiological solution.

In yet another embodiment of the composition comprising an alloplastic injectable suspension, the physiologically acceptable suspending agent comprises collagen. In a further embodiment, the collagen is derived from an animal. In a still further embodiment, the collagen is derived from a bird.

In another embodiment of the composition comprising an alloplastic injectable suspension, the collagen is genetically engineered in bacteria. In an embodiment, the bacteria may be any bacteria used for recombinant expression of proteins. The bacteria may be a *Streptococcus* strain in a further embodiment.

A method of making a composition comprising an alloplastic injectable suspension for use as a dermal filler comprising a biocompatible and pliable material and a physiologically acceptable suspending agent, said method comprising admixing a biocompatible and pliable material with a physiologically acceptable suspending agent is provided in an embodiment.

In an embodiment of this method, the biocompatible and pliable material is a copolymer of an unsubstituted acrylate monomer and a substituted acrylate monomer.

In a further embodiment of this method, the substituted acrylate monomer is substituted with a methyl group. In other embodiments of the copolymer of the unsubstituted acrylate monomer and the substituted acrylate monomer, the substituted acrylate monomer may be substituted with a functional group other than a methyl group. Substituent groups may include those groups that are unreactive (or potentially reactive group, but rendered inaccessible to reaction) and of the same or equivalent steric size as a methyl group, but the steric size of a substituent group may not be not limited to one similar to a methyl group. For example, other alkyl group derivatives, e.g., one to four, even five, carbon chain lengths (methyl, ethyl, propyl, isopropyl, butyl, tert-butyl and pentyl) acrylate derivatives, may be used as a substituent in place of a methyl group of the substituted acrylate monomer. In an alternative embodiment of the copolymer of an unsubstituted acrylate monomer and a substituted acrylate monomer, a substituent group for the substituted acrylate monomer may be chlorine or another halogen. A nitrile group may be another possible substituent for the substituted acrylate monomer. The substituted acrylate monomer may be substituted with a phenyl group, as described above.

In another embodiment of the method of making a composition comprising an alloplastic injectable suspension for use as a dermal filler, the biocompatible and pliable material is an acrylate/methacrylate copolymer. In a further embodiment of this method, the acrylate/methacrylate copolymer is a solid. In yet another embodiment, the solid acrylate/methacrylate copolymer may be a powder. In still another embodiment of this method, the solid may be a non-porous microbead. In another embodiment of this method, the solid may be a microsphere. In a further embodiment of the method of making an alloplastic injectable suspension for use as a dermal filler, the solid may have a diameter of about 10µ to about 100µ. According to another embodiment, the solid has a diameter of between about 0.01µ to about 10µ. In another embodiment, the solid has a diameter of between about 0.1µ to about 5µ.

In another embodiment of this method, the physiologically acceptable suspending agent is resorbable. In an embodiment, the physiologically acceptable suspending agent may be a buffered physiological solution. In yet another embodiment of this method, the physiologically acceptable suspending agent comprises cross-linked sodium hyaluronate. In another embodiment, the physiologically acceptable suspending agent comprises a non cross-linked sodium hyaluronate. In a further embodiment, the physiologically acceptable suspending agent comprises collagen. In an alternative embodiment, the collagen may be derived from an animal. In another alternative embodiment of this method, the collagen may be derived from a bird. In a still further embodiment of this method, the collagen may be genetically engineered in bacteria. In an embodiment, the bacteria may be any bacteria used for recombinant expression of proteins. The bacteria may be a *Streptococcus* strain in a further embodiment.

A method of augmenting soft tissue to provide long-term reduction of a skin defect, said method comprising stimulating collagen production, fibroblast production, fibrocyte production or production of any combination thereof, beneath the skin defect, is provided in an embodiment.

In further embodiment of this method of augmenting soft tissue to provide long-term reduction of a skin defect, the stimulation of collagen production fibroblast production, fibrocyte production or production of any combination thereof is effected by injecting into the deep reticular dermis a dermal filler, said dermal filler being a composition comprising an alloplastic injectable suspension and comprising a biocompatible and pliable material and a physiologically acceptable suspending agent.

In an embodiment of this method of augmenting soft tissue to provide long-term reduction of a skin defect, the biocompatible and pliable material is a copolymer of an unsubstituted acrylate monomer and a substituted acrylate monomer.

In a further embodiment of this method, the substituted acrylate monomer is substituted with a methyl group. In another embodiment of the copolymer of the unsubstituted acrylate monomer and the substituted acrylate monomer, the substituted acrylate monomer may be substituted with a functional group other than a methyl group. Substituent groups may include those groups that are unreactive (or potentially reactive group, which are rendered inaccessible to reaction) and of the same or equivalent steric size as a methyl group, but the steric size of a substituent group may not be not limited to one similar to a methyl group. For example, other alkyl group derivatives, e.g., one to four, even five, carbon chain lengths (methyl, ethyl, propyl, isopropyl, butyl, tert-butyl and pentyl) acrylate derivatives, may be used as a substituent in place of a methyl group of the substituted acrylate monomer. In an alternative embodiment of the copolymer of an unsubstituted acrylate monomer and a substituted acrylate monomer, a substituent group for the substituted acrylate monomer may be chlorine or another halogen. A nitrile group may be another possible substituent for the substituted acrylate monomer. The substituted acrylate monomer may be substituted with a phenyl group, as described above.

In another embodiment of the method of augmenting soft tissue to provide long-term reduction of a skin defect, the biocompatible and pliable material is an acrylate/methacrylate copolymer. In a further embodiment of this method, the acrylate/methacrylate copolymer is a solid. In yet another embodiment, the solid acrylate/methacrylate copolymer may be a powder. In still another embodiment of this method, the solid may be a non-porous microbead. In another embodiment of this method, the solid may be a microsphere. In a further embodiment of the method of augmenting soft tissue to provide long-term reduction of a skin defect, the solid may have a diameter of about 10µ to about 100µ.

According to further embodiments of the method for augmenting soft tissue to provide long-term reduction of a skin defect, the acrylate/methacrylate is in the form of finely ground solid particles having a diameter of less than about 100µ. According to an embodiment, the diameter of the finely ground solid particles is less than about 10µ. According to a preferred embodiment, the particles have a diameter of about 0.01µ to about 10µ. According to another preferred embodiment, the particles have a diameter of about 0,1µ to about 5µ.

In another embodiment of this method, the physiologically acceptable suspending agent is resorbable. In an embodiment, the physiologically acceptable suspending agent may be a buffered physiological solution. In yet another embodiment of this method, the physiologically acceptable suspending agent comprises cross-linked sodium hyaluronate. In another embodiment, the physiologically acceptable suspending agent comprises a non cross-linked sodium hyaluronate. In a further embodiment, the physiologically acceptable suspending agent comprises collagen. In an alternative embodiment, the collagen may be derived from an animal. In another alternative embodiment of this method, the collagen may be derived from a bird. In a still further embodiment of this method, the collagen may be genetically engineered in bacteria. In an embodiment, the bacteria may be any bacteria used for recombinant expression of proteins. The bacteria may be a *Streptococcus* strain in a further embodiment.

The dermal filler may be injected below the skin defect at a junction of the dermis and subcutaneous fat in an embodiment of this method augmenting soft tissue to provide long-term reduction of a skin defect. In another embodiment, the injected dermal filler produces little immunologic response in the host tissue or no immunologic response in the host tissue. In a further embodiment, the skin defect may be a result of loss of collagen and hyaluronic acid in the skin during the aging process. In an alternative embodiment, the skin defect may be a result of premature aging, said premature aging caused by overexposure to sunlight, overexposure to environmental pollutants, smoking tobacco products, exposure to cigarette smoke, poor nutrition and skin disorders.

In another embodiment of the method of augmenting soft tissue to provide long-term reduction of a skin defect, the skin defect may be a dynamic wrinkle, a fine wrinkles or a static wrinkle. In further alternative embodiments, the dynamic wrinkle may be a forehead crease, a brow burrow or an eye line (crow's feet). In a still further alternative embodiment, the static wrinkle may be a skin fold wrinkle resulting from sagging skin. In another embodiment, the skin defect is a medical condition selected from the group consisting of an acne scar, for example, a "rolling" scar, a "boxcar" scar or an "ice pick" scar, a surgical scar, trauma scar, a large pore and a soft tissue contour defect. In an embodiment, the medical condition is a deformity that requires re-contouring, such as a small tissue defect (e.g., after animal bite(s)) or a deformity related to trauma where the deformity is cosmetically unappealing. In a further embodiment of the method of augmenting soft tissue, the augmentation may be after plastic surgery to achieve symmetry or a desired result.

In a further embodiment of the method of augmenting soft tissue to provide long-term reduction of a skin defect, a "long-term" reduction of a skin defect is of a duration of at least one year. In another embodiment of this method, a long-term reduction of a skin defect is of a duration of from at least one year to about five years. In still another embodiment of this method, a long-term reduction of a skin defect is of a duration from about five years to about ten years. In yet another embodiment of this method, a long-term reduction of a skin defect is of a duration from about ten years or longer.

A method of reducing wrinkles and scars, said method comprising stimulating collagen production, fibroblast production, fibrocyte production or production of any combination thereof, beneath the skin defect, is further provided in another embodiment.

In an embodiment of this method of reducing wrinkles and scars, the biocompatible and pliable material is a copolymer of an unsubstituted acrylate monomer and a substituted acrylate monomer.

In a further embodiment of this method, the substituted acrylate monomer is substituted with a methyl group. In another embodiment of the copolymer of the unsubstituted acrylate monomer and the substituted acrylate monomer, the substituted acrylate monomer may be substituted with a functional group other than a methyl group. Substituent groups may include those groups that are unreactive (or potentially reactive group, but rendered inaccessible to reaction) and of the same or equivalent steric size as a methyl group, but the steric size of a substituent group may not be not limited to one similar to a methyl group. For example, other alkyl group derivatives, e.g., one to four, even five, carbon chain lengths (methyl, ethyl, propyl, isopropyl, butyl, tert-butyl and pentyl) acrylate derivatives, may be used as a substituent in place of a methyl group of the substituted acrylate monomer. In an alternative embodiment of the copolymer of an unsubstituted acrylate monomer and a substituted acrylate monomer, a substituent group for the substituted acrylate monomer may be chlorine or another halogen. A nitrile group may be another possible substituent for the substituted acrylate monomer. The substituted acrylate monomer may be substituted with a phenyl group, e.g., where no pi-stacking of the phenyl groups occurs.

In another embodiment of the method for reducing wrinkles and scars, the biocompatible and pliable material is an acrylate/methacrylate copolymer. In a further embodiment of this method, the acrylate/methacrylate copolymer is a solid. In yet another embodiment, the solid acrylate/methacrylate copolymer may be a powder. In still another embodiment of this method, the solid may be a non-porous microbead. In another embodiment of this method, the solid may be a microsphere. In a further embodiment of the method of reducing wrinkles and scars, the solid may have a diameter of about 10µ to about 100µ.

In accordance with further embodiment of the methods of the present invention, the acrylate/methacrylate copolymer is finely milled into particles each having a diameter less than about 100µ. In another embodiment, the particles each have a diameter of less than about 10µ. In another embodiment, the particles each have a diameter of about 0.01µ to about 10µ. In yet another embodiment, the particles each have a diameter of about 0.1µ to about 5µ. Based upon the guidance provided herein, a person skilled in the art would be able to prepare the finely milled copolymer in accordance with embodiments of the present invention using readily available techniques and equipment. For example, without limitation, mills that could be used to mill the copolymer in accordance with embodiments of the present invention include those manufactured by Fritsch and described at http://www.fritsch.de/en.html.

In another embodiment of this method, the physiologically acceptable suspending agent is resorbable. In an embodiment, the physiologically acceptable suspending agent may be a buffered physiological solution. In yet another embodiment of this method, the physiologically acceptable suspending agent comprises cross-linked sodium hyaluronate. In another embodiment, the physiologically acceptable suspending agent comprises a non cross-linked sodium hyaluronate. In a further embodiment, the physiologically acceptable suspending agent comprises collagen. In an alternative embodiment, the collagen may be derived from an animal. In another alternative embodiment of this method, the collagen may be derived from a bird. In a still further embodiment of this method, the collagen may be genetically engineered in bacteria. In an embodiment, the bacteria may be any bacteria used for recombinant expression of proteins. The bacteria may be a *Streptococcus* strain in a further embodiment.

In further embodiment of this method of reducing wrinkles and scars, the stimulation of collagen production fibroblast production, fibrocyte production or production of any combination thereof is effected by injecting into the deep reticular dermis a dermal filler, said dermal filler being alloplastic injectable suspension and comprising a biocompatible and pliable material and a physiologically acceptable suspending agent.

In another embodiment of the method of reducing wrinkles or scars, the dermal filler may be injected below the skin defect at a junction of the dermis and subcutaneous fat to provide a long-term reduction of the wrinkle or scar. In another embodiment of this method, the injected dermal filler produces little immunologic response in the host tissue or no immunologic response in the host tissue. In a further embodiment, the wrinkle or scar may be a result of loss of collagen and hyaluronic acid in the skin during the aging process. In an alternative embodiment, the wrinkle or scar may be a result of premature aging, said premature aging caused by overexposure to sunlight, overexposure to environmental pollutants, smoking tobacco products, exposure to cigarette smoke, poor nutrition and skin disorders.

In another embodiment of the method of reducing wrinkles or scars to provide long-term reduction of the wrinkle or scar, the wrinkle or scar may be a dynamic wrinkle, a fine wrinkles or a static wrinkle. In further alternative embodiments, the dynamic wrinkle may be a forehead crease, a brow burrow or an eye line (crow's feet). In a still further alternative embodiment, the static wrinkle may be a skin fold wrinkle resulting from sagging skin. In another embodiment, the wrinkle or scar is a medical condition selected from the group consisting of an acne scar, for example, a "rolling" scar, a "boxcar" scar or an "ice pick" scar, a surgical scar, trauma scar, a large pore and a soft tissue contour defect. In an embodiment, the medical condition is a deformity that requires re-contouring, such as a small tissue defect (e.g., after animal bite(s)) or a deformity related to trauma where the deformity is cosmetically unappealing. In a further embodiment of the method of reducing wrinkles or scars, the reduction of wrinkles or scars may be after plastic surgery to achieve symmetry or a desired result.

In a further embodiment of the method of reducing wrinkles or scars to provide long-term reduction of the wrinkle or scar, a "long-term" reduction of a the wrinkle or scar may be of a duration of at least one year. In another embodiment of this method, a long-term reduction of a the wrinkle or scar may be of a duration of from at least one year to about five years. In still another embodiment of this method, a long-term reduction of a the wrinkle or scar may be of a duration from about five years to about ten years. In yet another embodiment of this method, a long-term reduction of a the wrinkle or scar may be of a duration from about ten years or longer.

In accordance with further embodiments of the present invention, the present invention contemplates the use of any of the compositions described herein with other suitable compositions, including as mixtures or as separately administered substances, as would be recognized by persons skilled in the art based upon the guidance provided herein. According to further embodiments, the present invention contemplates the use of the compositions as medical devices or in conjunction with suitable medical devices, including implantable and non-implantable medical devices and the like, as would be understood by persons skilled in the art.

The following examples are illustrative, but not limiting, of the compositions and of the present invention. Other suitable modifications and adaptations as would be known to those skilled in the art, based upon the guidance provided herein, are within the spirit and scope of the embodiments.

Example 1

Reduction of Horizontal Forehead Lines

Twenty patients presenting with deep horizontal forehead lines, creases or wrinkles are treated with injections of alloplastic injectable suspension for use as a dermal filler comprising acrylate/methacrylate (A/M) copolymer powder (or non-porous microbeads or microspheres) and a cross-linked sodium hyaluronate, (or non-crosslinked sodium hyaluronate).

Light topical anesthetic is applied to the skin proximal to the horizontal forehead lines, creases or wrinkles to alleviate any discomfort during injection. A 30-, 27- or 26-gauge needle of a 0.5-inch length is used. The syringe contains 0.5 cc of the suspended A/M copolymer. Needle patency is verified by gently squeezing some of the suspended A/M copolymer out of the needle tip. The needle is inserted into the skin beneath and along the line of the forehead line, crease or wrinkle, with constant thumb pressure applied on the syringe. The injection is places deep intradermally into the reticular dermis just above the junction between the dermis and the subcutaneous fat. Resistance from the dermis will be experienced, however, if the needle is placed too deep, there will be little resistance from the fatty tissue.

Injection occurs in a tunneling technique, wherein the needle is moved back and forth horizontally just beneath the forehead line, crease or wrinkle, such that the injection occurs simultaneously with withdrawal of the needle. The gray needle should not show through the skin of the line. If injected superficially intradermally, the microbeads or microspheres will form small granules in a line akin to a strand of pearls within the line.

Evenly massage with a fingertip the injected and apply slight pressure to smooth out any detected lumps. Vigorous massage is not advisable, as it will spread the injected suspended A/M copolymer deeper into the tissue and result in loss of the intended effect.

In about three months, the diminished thickness of the dermis recovers its previous thickness. The thickness recovery may be determined mostly through the use of before and after photos, thus, the time period may vary from patient to patient.

A second injection of the suspended A/M copolymer may be placed on top of the first injection layer after a period of four weeks to four months. This additive effect may be used to achieve the desired result. Deeper forehead lines may require a second, third and fourth injection of the suspended A/M copolymer.

An amount of 0.5 cc of the suspended A/M copolymer will suffice for injection beneath a forehead line, crease or wrinkle, for example, a frontal furrow. A second injection, if needed, for example, to even the distribution of the first injected and implanted microbeads or microspheres, will inject about the same amount of the suspended A/M copolymer, or less, depending on the tissue response and the patient's desired result.

Side-effects of superficial injection are treated with corticosteroid cream or intradermal corticosteroid injections. Dermabrasion will remove intradermal granules of microbeads or microspheres. Because of the inert nature of the copolymer, it is not expected to form granules in powder form. If microbeads or microspheres are used, the microbeads or microspheres can be spread around through massage within a day or two after the injection to even the distribution. Therefore, clumping is not expected, since it results if there is an inflammatory reaction which aggregates the copolymer microbeads or microspheres together.

Within four weeks to four months of the last injection of the suspended A/M copolymer the skin comprising the forehead line, crease or wrinkle will be raised to the same level as the surrounding skin, such that the appearance of the forehead line, crease or wrinkle will be diminished or eliminated. The decrease of appearance or removal forehead line, crease or wrinkle is expected to be permanent, such as to last at least 18 months with no palpability or visibility, and from about five to about ten years. Muscle movement over a time period of from about five to about ten years may cause the injected A/M copolymer to deepen by $1/10$ of a millimeter. If a line, crease or wrinkle appears during this time, an injection of the suspended A/M copolymer is placed on top of the original (or last, if more than one were injected) injection of powder, microbeads or microspheres.

Example 2

Reduction of Glabellar Frown Lines

Glabellar frown lines form between the eyebrows in an almost vertical position proximal to each eyebrow. To test the decrease of the appearance of glabellar frown lines or eliminate them, twenty patients presenting with moderate or deep frown lines between the eyebrows are treated with an injection of alloplastic injectable suspension for use as a dermal filler comprising acrylate/methacrylate (A/M) copolymer powder (or non-porous microbeads or microspheres) and a buffered physiological solution (or cross-linked sodium hyaluronate, non-crosslinked sodium hyaluronate or collagen), as the site of the glabellar frown lines in accordance with the procedure described in Example 1.

An injection of 0.5 cc of the suspended A/M copolymer will suffice to treat both glabellar frown lines. The dermis is generally thick and the connective tissue beneath the glabellar frown lines provides good support for the injected suspended A/M copolymer. The injection should not be placed too far caudally, such as not at the lower or tail end of the respective glabellar frown line, as a lump may form. If deep lines exist at the glabellar frown lines, treatment is repeated, as described above. A thicker dermis beneath the glabellar frown line permits intradermal injection without the above-described side-effects.

Within four weeks to four months of the last injection of the suspended A/M copolymer the skin comprising glabellar frown line will be raised to the same level as the surrounding skin, such that the appearance of the previously existing glabellar frown lines will be diminished or eliminated. The decrease of appearance or removal of glabellar frown lines is expected to be permanent, such as to last at least 18 months with no palpability or visibility, and from about five to about ten years. Muscle movement over a time period of from about five to about ten years may cause the injected A/M copolymer to deepen by $1/10$ of a millimeter. If a glabellar frown line appears during this time, an injection of the suspended A/M copolymer is placed on top of the original (or last, if more than one were injected) injection of powder, microbeads or microspheres.

Example 3

Reduction of Nasolabial Folds

Nasolabial folds, or smile lines, extend from the corners of the nose, around the sides of mouth and down to the chin. To test the decrease of the appearance of nasolabial folds or eliminate them, twenty patients presenting with moderate to deep nasolabial folds are treated by injection of alloplastic injectable suspension for use as a dermal filler comprising acrylate/methacrylate (A/M) copolymer powder (or non-porous microbeads or microspheres) and a buffered physiological solution (or cross-linked sodium hyaluronate, non-crosslinked sodium hyaluronate or collagen), as the site of the nasolabial folds in accordance with the procedure described in Example 1, except that the injections are administered parallel and medially (at the middle) to the respective fold. During the first three days, the injected A/M suspension may be moved laterally (to the side) by movement of the facial muscles. Accordingly, the injection is administered directly beneath and 1-2 mm medially to the crease.

In patients with thin skin, the injection of the suspended A/M copolymer must not be too superficial. Otherwise, side-effects such as erythema, such as reddening will develop at the injection site and the A/M microbeads or microspheres will be visible as granules.

An injection of 0.5 cc of the suspended A/M copolymer will suffice to treat one nasolabial fold. Therefore, treatment of both nasolabial folds will require two syringes, each with 0.5 cc the suspended A/M copolymer. Nasolabial folds generally will require a second treatment with an injection of the alloplastic injectable suspension for use as a dermal filler comprising A/M copolymer powder (or non-porous microbeads or microspheres) and a buffered physiological solution.

Within four weeks to four months of the last injection of the suspended A/M copolymer the skin comprising the respective nasolabial fold will be raised to the same level as the surrounding skin, such that the appearance of the previously existing nasolabial fold will be diminished or eliminated. The decrease of appearance or removal of the nasolabial folds is expected to be permanent, such as to last at least 18 months with no palpability or visibility, and from about five to about ten years. Muscle movement over a time period of from about five to about ten years may cause the injected A/M copolymer to deepen by $1/10$ of a millimeter. If a nasolabial fold glabellar appears during this time, an injection of the suspended A/M copolymer is placed on top of the original (or last, if more than one were injected) injection of powder, microbeads or microspheres, followed by a second treatment three to four months after the first repeat treatment.

Example 4

Reduction of Depressed ("Rolling") Acne Scars

Twenty patients presenting with either shallow, mildly depressed or deep "rolling" scars, such as having smooth edges which appear similar to "rolling hills," or "boxcar" scars, such as having a cross-section akin to a box car, are treated by injection of alloplastic injectable suspension for use as a dermal filler comprising acrylate/methacrylate (A/M)

copolymer powder (or non-porous microbeads or microspheres) and a buffered physiological solution (or cross-linked sodium hyaluronate, non-crosslinked sodium hyaluronate or collagen), in accordance with the procedure described in Example 1, except that the treatment of the "rolling" acne scars is by injection of the suspension of the A/M copolymer from a distance of 5 to 10 mm, such as such distance away from the scar, and treatment of "boxcar" acne scars is by injection of the suspension of the A/M copolymer perpendicularly downward into the center of the scar.

The suspension of the A/M copolymer is implanted as superficially as possible because blanching of the darkened scars is desired. Blanching may be achieved by moving the injected suspension of the A/M copolymer with the fingernail.

Fresh scars should never be treated because treatment will be ineffective and the scar may exacerbated.

Scars which appear to look like "ice picks" may be treated as the aforementioned scars, but must be pre-treated before injection of the suspension of the A/M copolymer. Pre-treatment may involve punching and suturing or subcising with an appropriate blade or needle at a depth of about 1 mm. In contrast to the "rolling" and "boxcar" scars, thusly pretreated "ice pick" scars are filled with the suspension of the A/M copolymer within 3 to 8 days of pre-treatment upon decreased swelling and firm closing of the incision wound.

An injection of less than 0.1 cc of the suspended A/M copolymer will suffice to treat an acne scar. Acne scars may require a second treatment with an injection of the alloplastic injectable suspension for use as a dermal filler comprising A/M copolymer powder (or non-porous microbeads or microspheres) and a buffered physiological solution (or cross-linked sodium hyaluronate, non-crosslinked sodium hyaluronate or collagen) may achieve blanching of the scar in addition to the volume fill.

Within four weeks to four months of the last injection of the suspended A/M copolymer the skin comprising the respective acne scar will be raised to the same level as the surrounding skin, such that the appearance of the previously existing acne scar will be diminished or eliminated. The decrease of appearance or removal of the acne scar is expected to be permanent, such as to last at least 18 months with no palpability or visibility, and from about five to about ten years. If acne scars re-appear as darkened areas of the skin with a depression of the skin of at least a shallow rolling scar, the scar is treated with an injection of the suspended A/M copolymer, administered in the same manner as described above for the respective type of acne scar and placed on top of the original (or last, if more than one were injected) injection of powder, microbeads or microspheres. If the recurring appearance of the scar is not aesthetically pleasing, a second treatment of the reappeared scar, may follow three to four months after the first repeat treatment.

Example 5

Reduction of Surgical Scars or Trauma Scars

Twenty patients presenting with either shallow, mildly depressed or deep surgery scars or trauma scars, for example, from a cut with a sharp object, either accidental or self-inflicted, are treated by injection of alloplastic injectable suspension for use as a dermal filler comprising acrylate/methacrylate (A/M) copolymer powder (or non-porous microbeads or microspheres) and a buffered physiological solution (or cross-linked sodium hyaluronate, non-crosslinked sodium hyaluronate or collagen), as the site of the surgery scars or trauma scars in accordance with the procedure described in Example 1. Deeper injection site such as subcutaneous tissue and periostial tissue may be needed, depending on the severity of the scar. Larger amounts of the suspension will be needed to ameliorate the cosmetic deformities in these cases. These cases may require more injections than wrinkles to titrate the desired effect.

An injection of 0.1 cc or more of the suspended A/M copolymer will suffice to treat a surgical scar or trauma scar. Such scars, especially deep ones, may require a second treatment with an injection of the alloplastic injectable suspension for use as a dermal filler comprising A/M copolymer powder (or non-porous microbeads or microspheres) and a buffered physiological solution to achieve filling (and possible blanching) of the scar.

Within four weeks to four months of the last injection of the suspended A/M copolymer the skin comprising the surgical scar or trauma scar will be raised to the same level as the surrounding skin, such that the appearance of the previously existing surgical scar or trauma scar will be diminished or eliminated. The decrease of appearance or removal of the surgical scar or trauma scar is expected to be permanent, such as to last at least 18 months with no palpability or visibility, and from about five to about ten years. If a surgical scar or trauma scar re-appears, the scar is treated with an injection of the suspended A/M copolymer, administered in the same manner as described above for the initial treatment and is placed on top of the original (or last, if more than one were injected) injection of powder, microbeads or microspheres. If the recurring appearance of the scar is not aesthetically pleasing, a second treatment of the reappeared scar, may follow three to four months after the first repeat treatment.

Example 6

Reduction of Single Crow's Feet

Twenty patients presenting with single crow's feet (one on each sides, but not multiple crow's feet) are treated by injection of alloplastic injectable suspension for use as a dermal filler comprising acrylate/methacrylate (A/M) copolymer powder (or non-porous microbeads or microspheres) and a buffered physiological solution (or cross-linked sodium hyaluronate, non-crosslinked sodium hyaluronate or collagen), as the site of the single crow's feet in accordance with the procedure described in Example 1. The area where crow's feet form has thinner epidermis and dermis. Therefore, a smaller amount of the alloplastic injectable suspension may be injected.

An injection of 0.05 cc to 0.2 cc of the suspended A/M copolymer will suffice to treat a single crow's feet. Deep single crow's feet may require a second treatment with an injection of the alloplastic injectable suspension for use as a dermal filler comprising A/M copolymer powder (or non-porous microbeads or microspheres) and a buffered physiological solution to achieve filling of the single crow's feet.

Within four weeks to four months of the last injection of the suspended A/M copolymer the skin comprising the single crow's feet will be raised to the same level as the surrounding skin, such that the appearance of the previously existing single crow's feet will be diminished or eliminated. The decrease of appearance or removal of the single crow's feet is expected to be permanent, such as to last at least 18 months with no palpability or visibility, and from about five to about ten years. If a single crow's feet re-appears, as a result of muscle movement over time, the single crow's feet is treated with an injection of the suspended A/M copolymer, administered in the same manner as described above for the initial treatment and is placed on top of the original (or last, if more than one were injected) injection of powder, microbeads or microspheres. If the recurring appearance of the single crow's feet is not aesthetically pleasing, a second treatment of the reappeared scar, may follow three to four months after the first repeat treatment.

Example 7

Treatment of Other Skin Defects and Medical Conditions

Skin defects besides the aforementioned conditions are treated in accordance with the procedures described in Example 1 and modified, as needed, by one of skill, to effect the desired treatment.

The described method of treatment may be used for deformities that require re-contouring such as of a small tissue defect (e.g., after animal bite(s)), deformities related to trauma where the deformity is cosmetically unappealing, or for augmentation after plastic surgery to achieve symmetry or a desired result.

Although the invention has been described with reference to various embodiments and examples, those skilled in the art recognize that various modifications may be made to the invention without departing from the spirit and scope thereof.

All of the above U.S. patents, U.S. patent application publications, U.S. patent applications, foreign patents, foreign patent applications and non-patent publications referred to in this specification are incorporated herein by reference, in their entirety.

What is claimed is:

1. A composition comprising: an alloplastic injectable suspension for use as a dermal filler comprising a biocompatible and pliable material and a physiologically acceptable suspending agent; wherein the biocompatible and pliable material is a copolymer of phenylethyl acrylate and phenylethyl methacrylate.

2. The composition of claim 1, wherein the copolymer is a powder, a non-porous microbead, or a microsphere.

3. The composition of claim 1, wherein the copolymer is in the form of particles each having a diameter of about 10µ to about 100µ; about 0.01µ to about 10µ, or about 0.01µ to about 5µ.

4. The composition of claim 1, wherein the physiologically acceptable suspending agent is resorbable.

5. The composition of claim 4, wherein the physiologically acceptable suspending agent is a buffered physiological solution, cross-linked sodium hyaluronate, a non cross-linked sodium hyaluronate, isolated collagen, collagen isolated from an animal, collagen isolated from a bird, or genetically engineered collagen.

6. The composition of claim 1, wherein said composition further comprises a local anesthetic.

7. The composition of claim 1, wherein the phenylethyl acrylate and the phenylethyl methacrylate are present in the copolymer at a molar ratio of about 1:1000; about 1:100; about 1:10; about 1:9; about 1:8; about 1:7; about 1:6; about 1:5; about 1:4; about 1:3; about 1:2; or about 1:1.

8. The composition of claim 1, wherein said copolymer is cross-linked.

9. A method of making the composition of claim 1 comprising an alloplastic injectable suspension for use as a dermal filler comprising a biocompatible and pliable material and a physiologically acceptable suspending agent, comprising admixing a biocompatible and pliable material with a physiologically acceptable suspending agent; wherein the biocompatible and pliable material is a copolymer of phenyl ethyl acrylate and phenylethyl methacrylate.

10. The method of claim 9, wherein the copolymer is a powder, a non-porous microbead, or a microsphere.

11. The method of claim 10, wherein the copolymer is in the form of particles each having a diameter of about 10µ to about 100µ; about 0.01µ to about 10µ, or about 0.01µ to about 5µ.

12. The method of claim 9, wherein the phenylethyl acrylate and the phenylethyl methacrylate are present in the copolymer at a molar ratio of about 1:1000; about 1:100; about 1:10; about 1:9; about 1:8; about 1:7; about 1:6; about 1:5; about 1:4; about 1:3; about 1:2; or about 1:1.

13. The method of claim 9, wherein said copolymer is cross-linked.

14. A method of augmenting soft tissue to provide long-term reduction of a skin defect, said method comprising injecting into the deep reticular dermis the composition of claim 1.

15. The method of claim 14, wherein the injected dermal filler produces little immunologic response in the host tissue or no immunologic response in the host tissue.

16. The method of claim 14, wherein comprising injecting the dermal filler below the skin defect at a junction of the dermis and subcutaneous fat.

17. The method of claim 14, wherein the skin defect is a result of loss of collagen and hyaluronic acid in the skin during the aging process.

18. The method of claim 14, wherein the skin defect is a result of premature aging, said premature aging caused by overexposure to sunlight, overexposure to environmental pollutants, smoking tobacco products, exposure to cigarette smoke, poor nutrition and skin disorders.

19. The method of claim 14, wherein the skin defect is a dynamic wrinkle, a fine wrinkles or a static wrinkle.

20. The method of claim 14, wherein the skin defect is an acne scar, a surgical scar, a large pore, or a soft tissue contour defect.

21. The method of claim 14, wherein the long-term reduction of the skin defect is of a duration of at least one year.

* * * * *